United States Patent
Bae et al.

(10) Patent No.: US 9,603,891 B2
(45) Date of Patent: Mar. 28, 2017

(54) PEPTIDE COMPOUND FOR INHIBITING RESTENOSIS AND PROMOTING RE-ENDOTHELIALIZATION AND METHOD FOR PREPARING THE SAME

(71) Applicant: Chonnam National University Hospital, Gwangju (KR)

(72) Inventors: In-Ho Bae, Gwangju (KR); Dae Sung Park, Gwangju (KR); So Youn Lee, Gwangju (KR); Eun Jae Jang, Gwangju (KR); Kyung Seob Lim, Gwangju (KR); Myung Ho Jeong, Gwangju (KR)

(73) Assignee: Chonnam National University Hospital, Gwangju (KR)

( * ) Notice: Subject to any disclaimer, the term of this patent is extended or adjusted under 35 U.S.C. 154(b) by 0 days.

(21) Appl. No.: 14/741,949

(22) Filed: Jun. 17, 2015

(65) Prior Publication Data

US 2015/0368297 A1 Dec. 24, 2015

(30) Foreign Application Priority Data

Jun. 19, 2014 (KR) .................. 10-2014-0074700

(51) Int. Cl.
| | |
|---|---|
| *A61K 38/08* | (2006.01) |
| *C07K 7/06* | (2006.01) |
| *A61K 31/4745* | (2006.01) |
| *A61L 31/08* | (2006.01) |
| *A61L 31/16* | (2006.01) |
| *A61K 47/48* | (2006.01) |

(52) U.S. Cl.
CPC .......... *A61K 38/08* (2013.01); *A61K 31/4745* (2013.01); *A61L 31/08* (2013.01); *A61L 31/16* (2013.01); *C07K 7/06* (2013.01); *A61K 47/48246* (2013.01); *A61L 2300/412* (2013.01); *A61L 2300/606* (2013.01); *A61L 2400/18* (2013.01); *A61L 2420/00* (2013.01)

(58) Field of Classification Search
None
See application file for complete search history.

(56) References Cited

U.S. PATENT DOCUMENTS

2003/0224987 A1* 12/2003 Ryu .................. C07K 5/081
                                                                    514/2.4
2004/0117007 A1     6/2004 Whitbourne et al.

FOREIGN PATENT DOCUMENTS

KR      1020140038941 A      3/2014

OTHER PUBLICATIONS

The price list from EZbiolab, http://www.ezbiolab.com/peptide_modification.html, downloaded Jun. 14, 2016.*
Master Organic Chemistry (http://www.masterorganicchemistry.com/2014/11/19/ether-cleavage/, downloaded Jun. 20, 2016.*
Eun Jae Jang, "Bioactive Peptide-Coated Stent Promotes Endothelial Cell Proliferation and Prevents Stent Thrombosis" presented at the 15th Symposium of Society for Circulatory System and the 2nd Integrative Cardiovascular Imaging Symposium: May 24, 2014, Yonsei University.
Eun Jae Jang, "Bioactive Peptide-Coated Stent Promotes Endothelial Cell Proliferation and Prevents Stent Thrombosis" presented at the 25th Spring Symposium of Korean Society on Thrombosis and Hemostasis: May 19, 2014, Gyeongsang National University Hospital.
Solomons, "Organic Chemistry", 4th Ed., 1988, pp. 837-838; 855-856.

* cited by examiner

*Primary Examiner* — Fred Reynolds
(74) *Attorney, Agent, or Firm* — The Webb Law Firm

(57) ABSTRACT

Provided are a peptide compound prepared by additional synthesis in a drug having an effect of inhibiting restenosis, a composition for inhibiting restenosis and promoting re-endothelialization including the peptide compound, and a stent having a surface coated by using the composition, in order to overcome a restenosis problem in the stent.

1 Claim, 1 Drawing Sheet

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: proliferation-inducing peptide
```

```
<400> SEQUENCE: 1
Trp Lys Tyr Met Ile Arg Val
1               5
```

PEPTIDE COMPOUND FOR INHIBITING RESTENOSIS AND PROMOTING RE-ENDOTHELIALIZATION AND METHOD FOR PREPARING THE SAME

CROSS-REFERENCE TO RELATED APPLICATION

This application claims priority to Korean Patent Application No. 10-2014-0074700 filed Jun. 19, 2014, the disclosure of which is hereby incorporated in its entirety herein by reference.

REFERENCE TO A SEQUENCING LISTING

The Sequence Listing associated with this application is filed in electronic format via EFS-Web and is hereby incorporated by reference into the specification in its entirety. The name of the text file containing the Sequence Listing is 154859_ST25.txt. The size of the text file is 574 bytes, and the text file was created on Jan. 8, 2016.

TECHNICAL FIELD

The following disclosure relates to a peptide compound for inhibiting restenosis and promoting re-endothelialization and a method for preparing the same.

BACKGROUND

In accordance with the recent trend of an aging society, a coronary artery disease such as angina pectoris, myocardial infarction, or the like, has increased at a rapid rate in adults in Korea over the last 10 years, and is the highest cause of death except for cancer. The coronary artery disease is a disease that occurs in blood vessels surrounding the heart, and causes blood supply disorder in the heart muscle. The most common cause of the coronary artery disease is arteriosclerosis. When plaque made by a combination of cholesterol and other fats accumulate in coronary arteries, and various other components in blood are correspondingly increased, which cause coronary stenosis, and accordingly, blood supply to the heart muscle is reduced, which results in lack of nutrients and oxygen. As a result, it may cause chest pain (angina) or myocardial infarction, and even worse, lead to death.

Therefore, as a method of treating the diseases occurring in the blood vessels, a treatment method of expanding blood vessel passages narrowed due to stenosis by using an implantation tool called a stent has been generally and frequently used.

When stenosis or occlusion occurs in vascular or nonvascular lumen in a human body, the stent is a general term for medical devices for the purpose of opening the lumen. The stent was first suggested by Charles R. Stent at the end of the 19th Century, while stent implantation was first attempted in the peripheral artery by Charles Dotter in 1969, and a stent having a single spiral structure was invented by Maass in the 1980s.

The stent placement surgery using the stent is most common in terms of most treatment methods for a cardiovascular disease due to a low restenosis effect and a previously proven treatment effect, and usage frequency and reliability of the stent have continuously increased. In addition, recently, research into localization of a drug-eluting stent (DES) in the country has also been actively ongoing.

The drug-eluting stent (DES) in which a drug is directly delivered to a cell or a tissue by coating the drug on a surface of the stent so as to reduce restenosis in the stent was developed and usage thereof has been gradually increased.

However, after the stent placement surgery, damage occurs in the blood vessel which induce proliferation of smooth muscle cells according to an immune response to the stent at an initial induction, and problems such as in-stent restenosis (IRS) by smooth muscle cells proliferated in the blood vessels and acute thrombosis, late thrombosis, inflammation by a polymer used in coating, and the like occur.

Although a number of researches for solving the above-described problems have been conducted, most of them are to use drug coating technology for standardized drug controlled release capable of preventing restenosis, or is on the basis of inhibition of restenosis, and are limited to develop a drug coated stent simply controlling a drug in a continuous way rather than a coating technology for controlling a drug release according to a vascular therapy mechanism. Drugs currently used for commercially available DES are sirolimus or -limus family drugs that are a substitute for sirolimus, which are effective for inhibiting restenosis, but do not solve problems caused by DES usage, which is not sufficient in inhibiting inflammation, promoting re-endothelialization, inhibiting late thrombosis, and the like.

RELATED ART DOCUMENT (Patent Document 1) Korean Patent Laid-Open Publication No. KR 2014-0038941 A

SUMMARY

In order to overcome a restenosis problem in a stent, an embodiment of the present invention is directed to providing a novel peptide compound capable of promoting re-endothelialization in blood vessels by additional synthesis in a drug having an effect of inhibiting restenosis, and a stent having a surface coated by using the same.

In one general aspect, there is a peptide compound represented by Chemical Formula 1 below:

[Chemical Formula 1]

In another general aspect, a method for preparing a peptide compound includes:

reacting a compound represented by Chemical Formula 2 below with a compound represented by Chemical Formula 3 below to prepare a compound represented by Chemical Formula 4 below; and reacting the compound represented by Chemical Formula 4 below with a compound represented by Chemical Formula 5 below to prepare the compound represented by Chemical Formula 1 below:

[Chemical Formula 1]

-continued

[Chemical Formula 2]

[Chemical Formula 3]

HOOC-CH2-COOH (malonic acid)

[Chemical Formula 4]

[Chemical Formula 5]

WKYMIRV. (SEQ ID NO: 1)

In another general aspect, there is a composition for inhibiting restenosis and promoting re-endothelialization including a peptide compound represented by Chemical Formula 1 below:

In another general aspect, there is a stent including the composition for inhibiting restenosis and promoting re-endothelialization as described above.

[Chemical Formula 1]

The stent may be a stent for preventing or treating a cardiovascular disease.

DETAILED DESCRIPTION OF EMBODIMENTS

Figure 1:
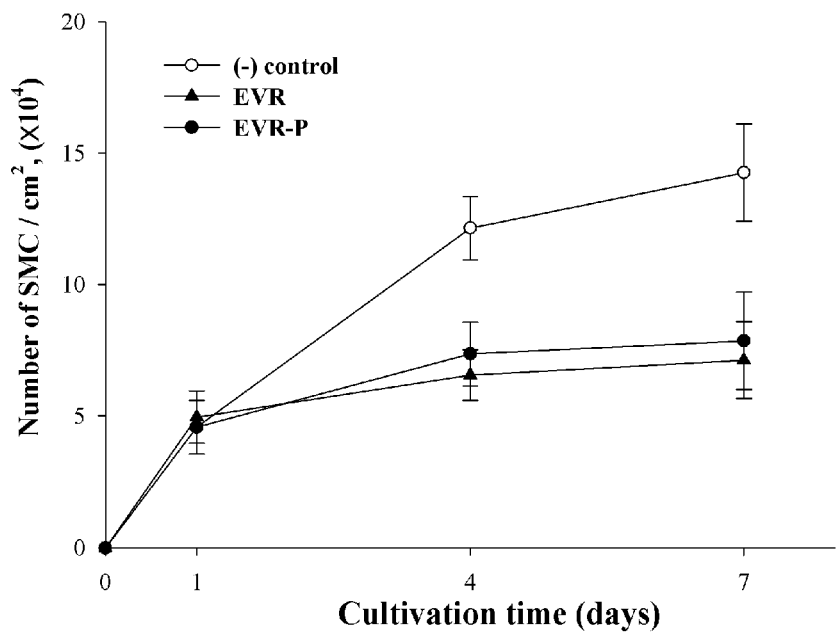
FIG. 1 is a graph showing an efficacy for inhibiting cell proliferation to vascular smooth muscle cell (SMC) of a peptide compound according to the present invention.

Hereinafter, the present invention will be described in more detail.

The present invention provides a novel peptide compound capable of inhibiting restenosis due to acute thrombosis easily occurring as a side effect after stent placement surgery in a human body and promoting re-endothelialization.

The novel peptide compound of the present invention is represented by Chemical Formula 1 below:

A peptide compound represented by Chemical Formula 1 above, having synthesized peptide having a sequence of WKYMIRV (SEQ ID NO: 1), according to an exemplary embodiment of the present invention may be synthesized by the following reaction.

A compound represented by Chemical Formula 4 below may be prepared by reacting Everolimus which is a compound represented by Chemical Formula 2 below with a malonic acid which is a compound represented by Chemical Formula 3 below to substitute an —OH group at the left end of the Everolimus with a carboxylic group.

A novel bidirectional functional compound which is the compound represented by Chemical Formula 1 may be synthesized by an amide bond (—CONH) which is a chemical bond formed by reacting the carboxylic group of the compound represented by Chemical Formula 4 and an amino group of the peptide, and therefore, NH of the compound represented by Chemical Formula 1 is provided by the reaction of the carboxylic group of the compound represented by Chemical Formula 4 and the amino group of the peptide.

[Chemical Formula 1]

The novel peptide compound represented by Chemical Formula 1 of the present invention is a compound having an efficacy for preventing the most common side effect after a stent implantation in a human body.

The peptide having a sequence of WKYMIRV (SEQ ID NO: 1) has an excellent effect in promoting endothelial cell proliferation and reinforcing functions of the endothelial cell.

Preferably, the peptide may be a peptide in which fluorophores are labeled on the peptide having a sequence of WKYMIRV (SEQ ID NO: 1).

The fluorophores are not limited, but may be used as long as it is capable of being labeled on the peptide. For example, cy5.5, Rhodamin, FITC, GFP may be used, and fluorescein isothiocyanate (FITC) among the fluorophores is the most preferred.

In addition, the present invention provides a method for preparing a peptide compound represented by Chemical Formula 1 below. According to an exemplary embodiment of the present invention, the method for preparing the peptide compound represented by Chemical Formula 1 below includes reacting the compound represented by Chemical Formula 2 below with the compound represented by Chemical Formula 3 below to prepare the compound represented by Chemical Formula 4 below; and reacting the compound represented by Chemical Formula 4 below with a compound represented by Chemical Formula 5 below to prepare the compound represented by Chemical Formula 1 below:

[Chemical Formula 1]

[Chemical Formula 2]

[Chemical Formula 3]

[Chemical Formula 4]

[Chemical Formula 5]

WKYMIRV. (SEQ ID NO: 1)

A solvent used in the preparation method of the present invention is not limited as long as it is a general organic solvent. For example, the solvent may be at least one kind selected from the group consisting of (C1-C10)polyol such as ethanol, methanol, isopropanol, or the like, normal hexane (n-hexane), cyclohexane, normal pentane (n-pentane), diethyl ether (ether), toluene, tetrahydrofuran (THF), dichloromethane (DCM), and trichloromethane (chloroform).

A reaction temperature in the preparation method of the present invention is not limited as long as it is a temperature used in general organic synthesis, but may vary according to a reaction time, an amount of a reaction material and a starting material. After complete consumption of the starting material is confirmed by NMR, GC, and the like, the reaction is completed. When the reaction is completed, the solvent may be removed by simple distillation under reduced pressure after filtration, and then a desired material may be separated and refined by general methods such as fractional distillation, or distillation under reduced pressure, and the like.

According to another embodiment, the present invention provides a composition for inhibiting restenosis and promoting re-endothelialization including the peptide compound.

The compound represented by Chemical Formula 2 used in the preparation method of the present invention is Everolimus which is one of the -limus family of immunosuppressive compounds developed by Novartis.

Everolimus, which is the -limus family drug currently mainly used for commercially available DES as a drug for treating a cardiovascular disease, which is represented by Chemical Formula 2, is effective for inhibiting restenosis, but is not sufficient for inhibiting inflammation, promoting re-endothelialization, inhibiting late thrombosis, and the like. Therefore, the present invention provides a composition for inhibiting restenosis and promoting re-endothelialization including the peptide compound capable of not only inhibiting restenosis, but also promoting re-endothelialization to inhibit late thrombosis by synthesizing the peptide which promotes re-endothelialization at the end of Everolimus represented by Chemical Formula 2.

Specifically, the novel peptide compound synthesized with the peptide having an effect of promoting proliferation of an endothelial cell and reinforcing function of the endothelial cell together with an efficacy of the existing Everolimus, that is an effect of inhibiting restenosis due to acute thrombosis may inhibit restenosis due to acute thrombosis which may occur after stent implantation in a human body and may promote re-endothelialization to prevent a delay of re-endothelialization formation caused by inflammation.

According to another embodiment, the present invention provides a stent including the composition for inhibiting restenosis and promoting re-endothelialization.

The stent having a surface coated by the novel peptide compound is a stent for inhibiting restenosis due to thrombosis that occurs after stent placement surgery in a human body and promoting re-endothelialization.

The stent used in the present invention is not specifically limited, but generally refers to an implantable structure such as an in-vivo implantable structure, an in-vivo implantable medical device, or the like, and means a stent usable for various purposes. As an example, the stent may be a stent for esophageal implantation used according to causes of stenosis of the esophagus or pylorus, gastroesophageal junction, or a stent for a cardiovascular disease which is implantable for a coronary artery disease or a cardiovascular disease, but is not specifically limited. The stent utilized for cardiovascular disease is preferred.

A material of the stent is also not limited, but may be a metal or a plastic.

The cardiovascular disease refers to diseases occurring in heart and major arteries. Major diseases of cardiovascular disease may be high blood pressure, ischemic heart disease, coronary artery disease, angina pectoris, myocardial infarction, atherosclerosis (arteriosclerosis), cerebrovascular disease, stroke, and arrhythmia, but the present invention is not specifically limited thereto.

Hereinafter, the present invention will be described in more detail with reference to the following exemplary embodiments. However, the following exemplary embodiments are provided by way of example, and therefore, the present invention is not limited thereto.

Example 1

Synthesis of Peptide Compound (EVR-P)

(1) Synthesis of Everolimus with COOH

A compound represented by Chemical Formula 4 above was synthesized by mixing Everolimus (LC Laboratories) as a starting material and malonic acid (Sigma-Aldrich) at a molar ratio of 1:1 to 2 and reacting and stirring the mixture in a methanol solvent at room temperature for 10 hours.

(2) Synthesis of Peptide Compound (EVR-P)

A peptide compound (EVR-P) was prepared by mixing the above-prepared peptide represented by Chemical Formula 4 and a peptide represented by Chemical Formula 5 at a molar ratio of 1:2 and reacting the mixture in a methanol solvent for 10 hours. For activation of the peptide compound (EVR-P), EDC(1-Ethyl-3-[3-dimethylaminopropyl]carbodiimide hydrochloride)(Sigma-Aldrich) and NHS(N-hydroxysulfosuccinimide) (Sigma-Aldrich) were added thereto, and additionally reacted at room temperature for 11 hours. The peptide compound (EVR-P) and EDC were mixed and reacted at a molar ratio of 1:3 m and the peptide compound (EVR-P) and NHS were mixed and reacted at a molar ratio of 1:3 to synthesize a final peptide compound (EVR-P).

Example 2

Cell Culture for Experiment Confirming Effect of Peptide Compound on Cell Proliferation An experiment confirming an effect of the compound prepared by Example 2 on a vascular smooth muscle cell (SMC), which is a main cause of restenosis occurring in blood vessels after stent implantation in a human body, and on a human umbilical vein endothelial cell (HUVEC), which is a cell for promoting vascular re-endothelialization, was conducted.

As cells used in a cell culture, the vascular smooth muscle cell (SMC) which is a smooth muscle cell, and the human umbilical vein endothelial cell (HUVEC) which is the cell for promoting vascular re-endothelialization were purchased from Korea Cell Line Bank, respectively. The cell culture was performed by culturing the vascular smooth muscle cell (SMC) and the human umbilical vein endothelial cell (HUVEC) in Dulbecoco's modified eagle medium (DMEM) with 10% fetal bovine serum (FBS) under conditions of 37° C. and 5% $CO_2$.

The cells were cultured in a disposable cell culture flask, and upon an experiment, the cells were cultured in the 24-well cell culture plate according to an experimental method.

Example 3

Effect of Peptide Compound on Proliferation of Vascular Smooth Muscle Cell (SMC)

An experiment for measuring restenosis inhibition and re-endothelialization promotion effects of the peptide compound prepared by Example 1 was conducted by using the vascular smooth muscle cell (SMC) which is a main cause of restenosis in cell proliferation. Results thereof were shown in FIG. 1.

$5 \times 10^4$ of SMC cells cultured according to Example 2 were cultured in the 24-well cell culture plate and then treated with 1 uM of the peptide compound prepared by Example 2 (hereinafter, referred to as 'EVR-P'). A group which was not treated with the compound was used as a positive control group (control). After treatment with the compound, 40 ul of XTT-regent (EZ-Cytox cell viability assay kit, Daeil Lab., Korea) was treated at 1, 4, and 7 days, respectively, and reacted for 2 hours. After the reaction, 200 ul of the culture medium was transferred from each well to a 96 well cell culture dish, and degree of color change was measured from absorbance at a 450 nm wavelength by a spectroscopy. Results thereof were shown in FIG. 1.

Example 4

Effect of Peptide Compound on Proliferation of Human Umbilical Vein Endothelial Cell (HUVEC)

Figure 2:
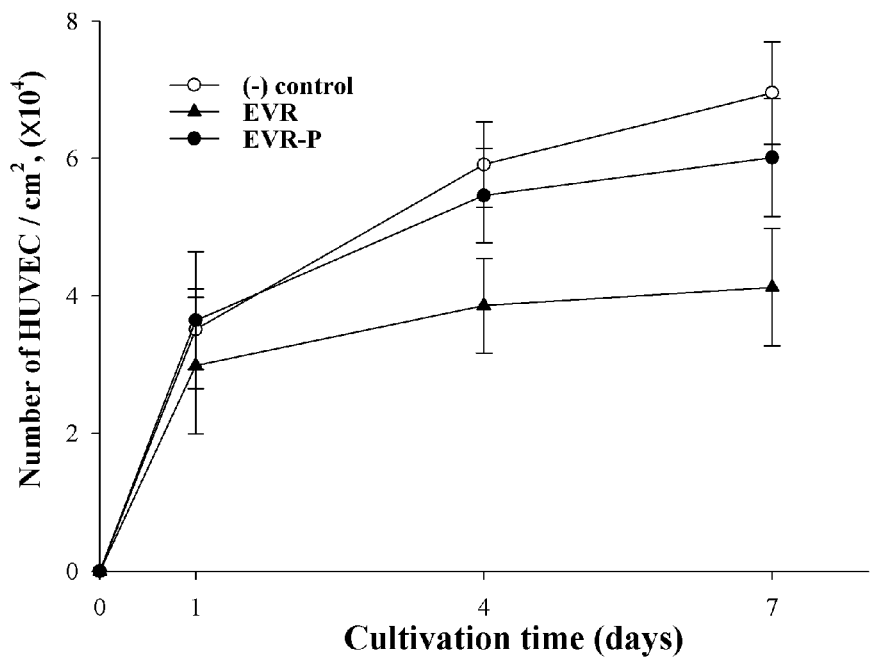
FIG. 2 is a graph showing an efficacy for promoting cell proliferation to human umbilical vein endothelial cell (HU-VEC) of the peptide compound according to the present invention.

An experiment for measuring restenosis inhibition and re-endothelialization promotion effects of the peptide compound prepared by Example 1 was conducted by using the human umbilical vein endothelial cell (HUVEC) which is a cell for promoting vascular re-endothelialization in cell proliferation. Results thereof were shown in FIG. 2.

$5 \times 10^4$ of HUVEC cells cultured according to Example 2 were cultured in the 24-well cell culture plate and then treated with 1 uM of the peptide compound (EVR-P) prepared by Example 1. A group which was not treated with the compound was used as a positive control group (control). After treatment with the compound, 40 ul of XTT-regent (EZ-Cytox cell viability assay kit, Daeil Lab., Korea) was treated at 1, 4, and 7 days, respectively, and reacted for 2 hours. After the reaction, 200 ul of the culture medium was transferred from each well to the 96 well cell culture dish, and degree of color change was measured by using absorbance at a 450 nm wavelength by a spectroscopy. Results thereof were shown in FIG. 2.

Comparative Example 1

Effect of Known Everolimus on SMC Proliferation $5 \times 10^4$ of SMC cells cultured according to Example 2 were cultured in the 24-well cell culture plate and then treated with 1 uM of the known Everolimus (EVR)(LC Laboratories). A group with non-treated cells was used as a positive control group (control). After treatment with the compound, 40 ul of XTT-regent (EZ-Cytox cell viability assay kit, Daeil Lab. Korea) was treated at 1, 4, and 7 days, respectively, and reacted for 2 hours. After the reaction, 200 ul of the culture medium was transferred from each well to the 96 well cell culture dish, and degree of color change was measured from absorbance at a 450 nm wavelength by a spectroscopy. Results thereof were shown in FIGS. 1 and 2.

Comparative Example 2

Effect of Known Everolimus on HUVEC Proliferation $5 \times 10^4$ of HUVEC cells cultured according to Example 2 were cultured in the 24-well cell culture plate and then treated with 1 uM of the known Everolimus (EVR)(LC Laboratories). A group with non-treated cells was used as a positive control group (control). After treatment with the compound, 40 ul of XTT-regent (EZ-Cytox cell viability assay kit, Daeil Lab. Korea) was treated at 1, 4, and 7 days, respectively, and reacted for 2 hours. After the reaction, 200 ul of the culture medium was transferred from each well to 96 well cell culture dish, and degree of color change was measured from absorbance at a 450 nm wavelength by a spectroscopy. Results thereof were shown in FIGS. 1 and 2.

Hereinafter, experimental results of Examples 3 and 4 and Comparative Examples 1 and 2 were explained as follows.

In comparison results between Example 3 according to the present invention and Comparative Example 1, the positive control group to which the compound according to Example 1 (EVR-P) was not added continuously grew until 7 days. Meanwhile, cell proliferation was inhibited in a case treated with EVR-P according to Example 3 and in a case treated with EVR according to Comparative Example 1. It was determined as a cell proliferation inhibition effect by mTOR binding domain of Everolimus. That is, when it was considered that the efficacy for inhibiting SMC proliferation of EVR-P prepared by the present invention was similar to Everolimus (EVR), it was confirmed that EVR-P which is a novel compound prepared by peptide synthesis using Everolimus (EVR) according to the present invention did not affect the efficacy for inhibiting muscle cell proliferation of the Everolimus (EVR).

In addition, in comparison results between Example 4 and Comparative Example 2, the positive control group to which EVR-P according to Example 1 was not added continuously grew until 7 days. Meanwhile, HUVEC cell proliferation was more improved in a case treated with EVR-P according to Example 4 as compared to a case treated with EVR according to Comparative Example 2. It indicated that proliferation of re-endothelialization is restored due to the EVR-P according to the present invention which is similar to the positive control group, and it proved that the peptide according to the present invention is a factor for promoting endothelial cell proliferation.

Therefore, it indicated that the peptide compound represented by Chemical Formula 1 prepared according to the present invention had an effect of inhibiting restenosis and promoting re-endothelialization.

According to the present invention, there are a peptide compound by additional synthesis in a drug having an effect of inhibiting restenosis, and a composition for inhibiting restenosis and promoting re-endothelialization including the peptide compound. Restenosis in the stent which is a problem of a drug-eluting stent (DES) may be inhibited and re-endothelialization may be promoted by coating the composition on the stent.

What is claimed is:
1. A peptide compound represented by Chemical Formula 1 below:
[Chemical Formula 1]
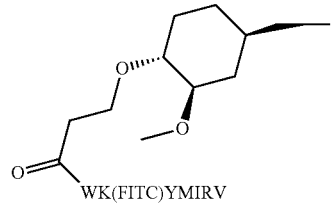
WK(FITC)YMIRV
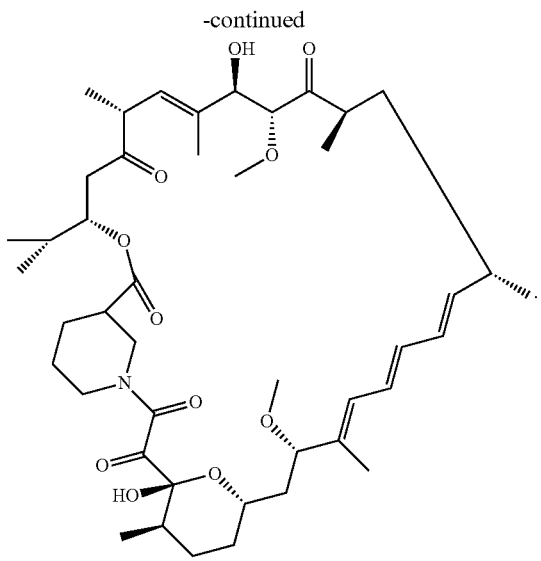
* * * * *